US009622962B2

(12) United States Patent
Lewus et al.

(10) Patent No.: US 9,622,962 B2
(45) Date of Patent: Apr. 18, 2017

(54) ORAL CARE PRODUCT AND METHODS OF USE AND MANUFACTURE THEREOF

(75) Inventors: Catherine Lewus, Denville, NJ (US); Gregory Szewczyk, Flemington, NJ (US); Sarita Mello, North Brunswick, NJ (US); Kimdra Smith-Webster, Williamstown, NJ (US); Jason Nesta, Cedar Knolls, NJ (US); Rensl Dillon, Ewing, NJ (US); Evangelia S. Arvanitidou, Princeton, NJ (US); Christine Cuiule, Mount Laurel, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/884,051

(22) PCT Filed: Nov. 12, 2010

(86) PCT No.: PCT/US2010/056514
§ 371 (c)(1),
(2), (4) Date: May 8, 2013

(87) PCT Pub. No.: WO2012/064339
PCT Pub. Date: May 18, 2012

(65) Prior Publication Data

US 2013/0236400 A1 Sep. 12, 2013

(51) Int. Cl.

| | |
|---|---|
| ***A61K 8/92*** | (2006.01) |
| ***A61K 8/368*** | (2006.01) |
| ***A61K 8/21*** | (2006.01) |
| ***A61K 8/49*** | (2006.01) |
| ***A61K 8/55*** | (2006.01) |
| ***A61Q 11/00*** | (2006.01) |
| ***A61K 8/03*** | (2006.01) |
| ***A61K 8/31*** | (2006.01) |
| ***A61K 8/34*** | (2006.01) |
| ***A61K 8/36*** | (2006.01) |
| ***A61K 8/37*** | (2006.01) |

(52) U.S. Cl.
CPC ................. *A61K 8/92* (2013.01); *A61K 8/03* (2013.01); *A61K 8/21* (2013.01); *A61K 8/31* (2013.01); *A61K 8/345* (2013.01); *A61K 8/36* (2013.01); *A61K 8/368* (2013.01); *A61K 8/37* (2013.01); *A61K 8/49* (2013.01); *A61K 8/55* (2013.01); *A61Q 11/00* (2013.01)

(58) Field of Classification Search
None
See application file for complete search history.

(56) References Cited

U.S. PATENT DOCUMENTS

| | | | | |
|---|---|---|---|---|
| 3,535,421 | A | 10/1970 | Briner et al. | |
| 3,678,154 | A | 7/1972 | Widder et al. | |
| 3,696,191 | A | 10/1972 | Weeks | |
| 3,991,177 | A | 11/1976 | Vidra et al. | |
| 4,058,595 | A | 11/1977 | Colodney | |
| 4,154,815 | A | 5/1979 | Pader | |
| 4,355,022 | A | 10/1982 | Rabussay | |
| 4,885,155 | A | 12/1989 | Parran, Jr. et al. | |
| 4,992,420 | A | 2/1991 | Neeser | |
| 5,000,939 | A | 3/1991 | Dring et al. | |
| 5,084,268 | A * | 1/1992 | Thaler | A61K 8/22 424/53 |
| 5,283,056 | A | 2/1994 | Chung et al. | |
| 5,560,906 | A * | 10/1996 | Scodari et al. | 424/54 |
| 5,624,906 | A * | 4/1997 | Vermeer | A61K 8/60 514/23 |
| 8,501,161 | B2 | 8/2013 | Prencipe et al. | |
| 2003/0072719 | A1 | 4/2003 | Nelson et al. | |
| 2004/0071769 | A1* | 4/2004 | Farng et al. | 424/450 |
| 2006/0286044 | A1* | 12/2006 | Robinson | A61K 8/345 424/49 |
| 2008/0213450 | A1* | 9/2008 | Williams | A23L 2/44 426/532 |
| 2008/0234173 | A1 | 9/2008 | Warr et al. | |
| 2009/0035229 | A1 | 2/2009 | Eirew | |
| 2009/0311200 | A1* | 12/2009 | Lambert | A61K 8/03 424/52 |
| 2010/0055138 | A1 | 3/2010 | Margulies et al. | |

FOREIGN PATENT DOCUMENTS

| | | |
|---|---|---|
| CN | 1977801 | 6/2007 |
| EP | 1797860 | 6/2007 |
| JP | H05-262631 | 10/1993 |
| RU | 2125440 | 1/1999 |

(Continued)

OTHER PUBLICATIONS

Silje Storehagen, Nanna Ose and Shilpi Midha. Dentifrices and Mouthwashes Ingredients and Their Use. Master's Thesis, Section of Dental Pharmacology and Pharmacotherapy, Dept. of Clinical Dentistry. University of Oslo. 2003.*

Merck Index Online entry for Potassium Sorbate (downloaded Feb. 20, 2016, from the website: https://www.rsc.org/Merck-Index/monograph/m10117/sorbic%20acid%20derivative%20potassium%20salt?q=authorize).*

Anonymous, 2008, "Ingredient Combinations in Two Phase Oral Rinse Preparations," Research Disclosure 530(19):486.

Gottschalck et al., eds., 2008, "Potassium Sorbate," International Cosmetic Ingredient Dictionary and Handbook, 12th ed., 2:2177.

(Continued)

*Primary Examiner* — Isaac Shomer
*Assistant Examiner* — Michael P Cohen

(57) ABSTRACT

This invention relates to a dual phase mouthwash comprising a hydrophilic phase, a hydrophobic phase, and a hydrotrope, wherein the hydrophilic phase comprises an effective amount of a preservative selected from methylisothiazolinone, sodium benzoate, potassium sorbate, and combinations thereof, as well as to methods of using and of making such compositions.

9 Claims, No Drawings

(56) References Cited

FOREIGN PATENT DOCUMENTS

| | | |
|---|---|---|
| RU | 2272636 | 3/2006 |
| WO | WO 99/51093 | 10/1999 |
| WO | WO 2009/152507 | 12/2009 |
| WO | WO 2010/014614 | 2/2010 |

OTHER PUBLICATIONS

Gottschalck et al., eds., 2008, "Sodium Benzoate," International Cosmetic Ingredient Dictionary and Handbook, 12th ed., 2:2489-2490.
Gottschalck et al., eds., 2008, "Sorbic Acid," International Cosmetic Ingredient Dictionary and Handbook, 12th ed., 2:2618.
International Search Report and Written Opinion in International Application No. PCT/US10/056514, mailed Oct. 20, 2011.
Lesnoy Balsam, 2008, "Mouth Rinse," Mintel GNPD No. 982553.
Wikipedia, 2011, "Hydrotrope," retrieved from internet Jul. 12, 2012, en.wikipedia.org/wiki/Hydrotrope, pp. 1-2.
Written Opinion in International Application No. PCT/US10/056514, mailed Dec. 12, 2012.
Fedotov, 2007, Great Dictionary of Medical Terms, p. 340.
Anonymous: "Sodium Benzoate I How to Prevent Aging and Cancer, HealthStyle TV", Jun. 15, 2009 (Jun. 15, 2009), XP055325828, Retrieved from the Internet: URL:https://thehealthreporter.tv/2009/06/15/how-toprevent-aging-and-cancer-sodium-benzoate/ [retrieved on Dec. 5, 2016].

* cited by examiner

ORAL CARE PRODUCT AND METHODS OF USE AND MANUFACTURE THEREOF

FIELD OF THE INVENTION

This invention relates to a preservative system for dual phase mouthwash composition comprising (i) a hydrophilic phase including a hydrotrope, (ii) a hydrophobic phase, and (iii) a preservative selected from methylisothiazolinone, sodium benzoate, and potassium sorbate and combinations thereof, as well as to methods of using and of making these compositions.

BACKGROUND OF THE INVENTION

Because of their high water content, mouthwashes present particular challenges in preventing microbial contamination. Dual phase mouthwashes present particular challenges in that the hydrophilic and hydrophobic phases should remain separated and form a temporary emulsion when mixed. The emulsion spontaneously reverts back to the two original phases after rest, without the formation of an emulsion. See, e.g., U.S. Patent Publication 20090311200, the contents of which are incorporated herein by reference. Selection of a preservative which is both effective and which does not impair the physical properties of the dual phase formulation is not trivial. Additionally, some preservatives negatively affect the taste or aesthetics of the product. Finally, conventional agents such as ethanol and paraben preservatives may be undesirable for certain indications or in particular markets.

Accordingly, there is a need to identify improved preservative agents for use in dual phase mouthwashes.

BRIEF SUMMARY OF THE INVENTION

It is now surprisingly discovered that dual phase mouthwashes comprising (i) a hydrophilic phase including a hydrotrope, (ii) a hydrophobic phase, and (iii) a preservative selected from methylisothiazolinone, sodium benzoate, and potassium sorbate and combinations thereof, are stable and effective.

The invention thus encompasses oral care compositions and methods of using the same that are effective in inhibiting or reducing the accumulation of plaque, reducing levels of acid producing (cariogenic) bacteria, remineralizing teeth, and inhibiting or reducing gingivitis. The invention also encompasses compositions and methods to clean the oral cavity and provide improved methods of promoting oral health and/or systemic health, including cardiovascular health, e.g., by reducing potential for systemic infection via the oral tissues.

The invention thus provides a mouthwash composition (a Composition of the Invention), comprising (i) a hydrophilic phase including a hydrotrope, (ii) a hydrophobic phase, and (iii) a preservative selected from methylisothiazolinone, sodium benzoate, potassium sorbate, and combinations thereof.

The Compositions of the Invention may comprise additional ingredients, e.g., selected from one or more of water, surfactants, solvents, vitamins, minerals, polymers, enzymes, humectants, thickeners, additional antimicrobial agents, additional preservatives, flavorings, colorings and/or combinations thereof. In particular embodiments, the invention may comprise an anti-calculus agent for example polyphosphate, e.g., pyrophosphate, tripolyphosphate, or hexametaphosphate, e.g., in alkali, e.g., sodium or potassium salt form, and/or may comprise a synthetic anionic polymeric polycarboxylate, such as 1:4 to 4:1 copolymers of maleic anhydride or acid with another polymerizable ethylenically unsaturated monomer, for example a co-polymer of methyl vinyl ether/maleic anhydride.

Effective amounts for the preservatives in the Compositions of the Invention, separately or in combination, are, for example, as follows, by weight: MIT: less than 0.1%, e.g., 0.0005-0.1%, e.g. 0.001%, 0.01% or 0.05%; sodium benzoate less than 1%, e.g. 0.1-0.5%, e.g., 0.11% or 0.44%; potassium sorbate less than 1%, e.g. 0.05%-0.5%, e.g., 0.1%.

The invention further encompasses methods comprising applying compositions effective upon application to the oral cavity, e.g., rinsing the oral cavity, optionally in conjunction with brushing, to (i) reduce or inhibit formation of dental caries, (ii) reduce or inhibit demineralization and promote remineralization of the teeth, (iii) reduce hypersensitivity of the teeth, (iv) reduce or inhibit gingivitis, (v) promote healing of sores or cuts in the mouth, (vi) reduce levels of acid producing bacteria, (vii) to increase relative levels of arginolytic bacteria, (viii) inhibit microbial biofilm formation in the oral cavity, (ix) raise and/or maintain plaque pH at levels of at least pH 5.5 following sugar challenge, (x) reduce plaque accumulation, (xii) treat, relieve or reduce dry mouth, (xii) clean the teeth and oral cavity (xiii) reduce erosion, (xiv) whiten teeth, (xv) immunize the teeth against cariogenic bacteria; and/or (xvi) promote systemic health, including cardiovascular health, e.g., by reducing potential for systemic infection via the oral tissues.

DETAILED DESCRIPTION OF THE INVENTION

The invention thus provides, in a first embodiment, a dual phase mouthwash (Composition 1.0), comprising a hydrophilic phase including a hydrotrope, a hydrophobic phase, and an effective amount of a preservative selected from methylisothiazolinone, sodium benzoate, potassium sorbate, and combinations thereof.

For example, any of the following compositions:

1.0.1. Composition 1.0 wherein the wherein hydrophobic and hydrophilic phases spontaneously separate following mixing of the phases and are substantially non-emulsified at room temperature one hour following mixing.

1.0.2. Any of the foregoing compositions wherein the hydrotrope component of the hydrophilic phase comprises a polyglycol, a polyhydric alcohol, or a mixture thereof.

1.0.3. Any of the foregoing compositions wherein the hydrotrope component comprises ethylene glycol, propylene glycol, glycerin, diethylene glycol, di-propylene glycol, tripropylene glycol, xylene glycol, 1,3-butylene glycol, 1,4-butylene glycol, 1,2,6-hexanetriol, sorbitol, xylitol, or a combination thereof.

1.0.4. Any of the foregoing compositions wherein the hydrotrope component comprises glycerin and/or propylene glycol.

1.0.5. Any of the foregoing compositions wherein the hydrotrope component comprises sorbitol.

1.0.6. Any of the foregoing compositions wherein the hydrophobic phase comprises an oil selected from isopropyl myristate, mineral oil, an edible oil, and combinations thereof.

1.0.7. Any of the foregoing compositions comprising from 1% to 90% by volume of the hydrophilic phase.

1.0.8. Any of the foregoing compositions having a 15:85 hydrophobic to hydrophilic weight ratio.

1.0.9. Any of the foregoing compositions wherein the hydrophilic phase comprises the hydrotrope component.

1.0.10. Any of the foregoing compositions which is substantially free of a cationic surfactant.

1.0.11. Any of the foregoing compositions wherein the preservatives are present, separately or in combination, in amounts by weight: MIT: less than 0.1%, e.g., 0.0005-0.1%, e.g. 0.001%, 0.01% or 0.05%; sodium benzoate less than 1%, e.g. 0.1-0.5%, e.g., 0.11% or 0.44%; potassium sorbate less than 1%, e.g. 0.05%-0.5%, e.g., 0.1%.

1.0.12. The foregoing composition wherein the preservative comprises sodium benzoate.

1.0.13. The foregoing composition wherein the preservative comprises sodium benzoate and potassium sorbate.

1.0.14. The foregoing composition comprising (i) 0.05%-0.5% sodium benzoate and (ii) 0.05%-0.2% potassium sorbate and/or 0.0005%-0.01% MIT.

1.0.15. Any of the foregoing compositions wherein the hydrophilic phase further comprises cetyl pyridinium chloride, e.g., in an amount of from 0.01-0.1%, e.g., 0.05%.

1.0.16. Any of the foregoing compositions wherein the hydrophilic phase further comprises an acid, e.g. an organic acid, e.g., citric acid.

1.0.17. Any of the foregoing compositions further comprising an anti-calculus agent for example polyphosphate, e.g., pyrophosphate, tripolyphosphate, or hexametaphosphate, e.g., in salt form, e.g., sodium or potassium salt form, e.g., in an amount of from 0.1-3%.

1.0.18. The foregoing composition wherein the anti-calculus agent is a pyrophosphate selected from tetrasodium pyrophosphate and tetrapotassium pyrophosphate and mixtures thereof.

1.0.19. The foregoing composition comprising 0.1 to 1% tetrasodium pyrophosphate and 1-2% tetrapotassium pyrophosphate, e.g. 0.25-0.75% tetrasodium pyrophosphate and 1.0-1.5% tetrapotassium pyrophosphate.

1.0.20. Any of the preceding compositions comprising at least one polymer selected from polyethylene glycols; synthetic anionic polymeric polycarboxylate, such as polyvinylmethyl ether maleic acid copolymers; polysaccharides (e.g., cellulose derivatives, for example carboxymethyl cellulose or polysaccharide gums, for example xanthan gum or carrageenan gum); and combinations thereof.

1.0.21. Any of the foregoing compositions comprising a synthetic anionic polymeric polycarboxylate, e.g., in an amount of 1-10%, e.g., 2.5-7.5%.

1.0.22. The foregoing composition wherein the synthetic anionic polymeric polycarboxylate is a 1:4 to 4:1 copolymer of maleic anhydride or acid with another polymerizable ethylenically unsaturated monomer, e.g. methyl vinyl ether/maleic anhydride having a molecular weight (M.W.) of 30,000 to 5,000,000 daltons, for example 1000 kD-3000 kD.

1.0.23. The foregoing composition comprising a co-polymer of methyl vinyl ether/maleic anhydride having the general structure $\left[ CH_2—CH(OCH_3)—CH(COOH)—CH(COOH) \right]_n$, viscosity of CP at 25° C. of 1-3 kCP, e.g., $1.7\times10^3$ CP, and nominal molecular weight of 1000 kD-3000 kD, e.g., $1.98\times10^6$, for example in an amount by weight of 1-10%, e.g., 5%

1.0.24. Any of the foregoing compositions which is ethanol-free.

1.0.25. Any of the foregoing compositions further comprising a basic amino acid in free or salt for, for example arginine, for example in an amount of 0.1-3%, e.g. 0.8%, 1.0.26. Any of the foregoing compositions further comprising a soluble calcium salt, e.g., selected from calcium glycerophosphate and salts of soluble carboxylic acids, and mixtures thereof, e.g., wherein the calcium salt is selected from calcium citrate, calcium malate, calcium lactate, calcium formate, calcium fumarate, calcium gluconate, calcium lactate gluconate, calcium aspartate, and calcium propionate, and mixtures thereof.

1.0.27. Any of the preceding compositions further comprising a fluoride source, e.g., a fluoride salt, for example sodium fluoride, or wherein the fluoride is covalently bound to another atom, e.g., a monofluorophosphate, for example sodium monofluorophosphate, a fluorosilicate, e.g., sodium fluorosilicate or ammonium fluorosilicate, or a fluorosulfate, e.g., hexafluorosulfate, amine fluoride and combinations thereof.

1.0.28. The preceding composition wherein the fluoride salt is present in an amount to provide 100 to 250 ppm available fluoride.

1.0.29. Any of the preceding compositions comprising sodium fluoride in an amount of 0.01-0.1%, e.g., 0.05%.

1.0.30. Any of the preceding compositions wherein the pH is between 5 and 6.5, e.g. 5.5.

1.0.31. Any of the preceding compositions further comprising an abrasive or particulate.

1.0.32. Any of the preceding compositions comprising a nonionic surfactant, e.g., in an amount of from 0.5-5%, for example 1-2%, selected from polaxamers (e.g., polaxamer 407), polysorbates (e.g., polysorbate 20), polyoxyl hydrogenated castor oil (e.g., polyoxyl 40 hydrogenated castor oil), and mixtures thereof.

1.0.33. Any of the preceding compositions comprising at least one humectant.

1.0.34. Any of the preceding compositions comprising at least one humectant selected from glycerin, sorbitol, propylene glycol, and combinations thereof, e.g., in a total amount of 10-40%.

1.0.35. Any of the preceding compositions comprising polymer films.

1.0.36. Any of the preceding compositions comprising flavoring, fragrance and/or coloring.

1.0.37. Any of the preceding compositions comprising at least 50% water.

1.0.38. Any of the preceding compositions comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions (e.g., zinc salts, for example zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.0.39. Any of the preceding compositions comprising an antioxidant, e.g., selected from the group consisting of Co-enzyme Q10, PQQ, Vitamin C, Vitamin E, Vitamin A, anethole-dithiothione, and mixtures thereof.

1.0.40. Any of the preceding compositions comprising a whitening agent.

1.0.41. Any of the preceding compositions comprising a whitening agent selected from a whitening active selected from the group consisting of peroxides, metal chlorites, perborates, percarbonates, peroxyacids, hypochlorites, and combinations thereof 1.0.42. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.0.43. Any of the preceding compositions further comprising an agent that interferes with or prevents bacterial attachment, e.g., solbrol or chitosan.

1.0.44. Any of the preceding compositions further comprising a physiologically acceptable potassium salt, e.g., potassium nitrate or potassium chloride, in an amount effective to reduce dentinal sensitivity.

1.0.45. Any of the preceding compositions comprising from 0.01% to 1% of a physiologically acceptable potassium salt, e.g., potassium nitrate and/or potassium chloride.

1.0.46. Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.0.47. A composition obtained or obtainable by combining the ingredients as set forth in any of the preceding compositions.

Levels of active ingredients will vary based on the nature of the delivery system and the particular active. For example, the zinc salt may be present at levels from, e.g., 0.05 to 2 wt %, e.g., 0.1 to 1 wt %. Fluoride may be present at levels of, e.g., 25 to 250 ppm, or up to 10× higher for a professional or prescription treatment product. Levels of additional antibacterial will vary similarly, depending on the agent used. For example, a triclosan mouthrinse may contain, e.g., 0.03 wt % triclosan.

In another embodiment, the invention encompasses a method to improve oral health comprising applying an effective amount of the oral composition of any of the embodiments set forth above to the oral cavity of a subject in need thereof, e.g., a method to i. reduce or inhibit formation of dental caries,
ii. reduce, repair or inhibit early enamel lesions, e.g., as detected by quantitative light-induced fluorescence (QLF) or electrical caries measurement (ECM),
iii. reduce or inhibit demineralization and promote remineralization of the teeth,
iv. reduce hypersensitivity of the teeth,
v. reduce or inhibit gingivitis,
vi. promote healing of sores or cuts in the mouth,
vii. inhibit microbial biofilm formation in the oral cavity,
viii. raise and/or maintain plaque pH at levels of at least pH 5.5 following sugar challenge,
ix. reduce plaque accumulation,
x. treat dry mouth,
xi. enhance systemic health, including cardiovascular health, e.g., by reducing potential for systemic infection via the oral tissues,
xii. whiten teeth,
xiii. reduce erosion of the teeth,
xiv. immunize (or protect) the teeth against cariogenic bacteria and their effects, and/or
xv. clean the teeth and oral cavity.

The invention further comprises the use of any of methylisothiazolinone, sodium benzoate, potassium sorbate and combinations thereof in the manufacture of a Composition of the Invention, e.g., for use in any of the indications set forth in the above method.

The compositions of the present invention comprise a hydrophilic and a hydrophobic phase, and a hydrotrope component which when mixed form a temporary oil-in-water emulsion, which breaks down and separates back into the hydrophobic and hydrophilic phases within 5 seconds to one hour following mixing. It has been surprisingly determined that the separation of the hydrophilic and hydrophobic phases is complete, e.g., with no emulsion existing between the two phases. Without intending to be bound by theory, it is believed that the high HLB of the hydrophobic phase allows for the complete separation of the two phases.

The hydrophobic phase of the composition of the present invention may contain any orally acceptable hydrophobic liquid, e.g., generally recognized as safe. Such materials are known in the art, and may include isopropyl myristate, liquid paraffin (mineral oil), edible oils such as olive oil, corn oil, coconut oil, soybean oil, and combinations thereof. A preferred hydrophobic phase comprises liquid paraffin, isopropyl myristate. Preferably, the hydrophobic phase has a HLB of from 7 to 12, e.g., 10.

The hydrophilic phase of the compositions of the present invention are aqueous based, e.g., having from 40% to 95% by weight water. Other useful materials may also include orally acceptable alcohols, humectants, or polymers. A humectant on a pure humectant basis, generally includes 10% to 50% in one embodiment or 15% to 25% in another embodiment by weight of the mouth wash composition. The hydrophilic phase may optionally include one or more polymers, e.g., in the hydrophilic phase, such as polyvinylmethyl ether maleic acid copolymers, polysaccharides (e.g. cellulose derivatives, for example carboxymethyl cellulose, or polysaccharide gums, for example xanthan gum or carrageenan gum). The compositions of the present invention may contain an orally acceptable polyvinylmethylether/maleic anhydride (PVME/MA) copolymer. The PVME/MA copolymer is present from 0.1% to 20%, for example 0.5% to 10% by weight. Generally the methyl vinyl ether to maleic anhydride ratio in the copolymer is 1:4 to 4:1, and the copolymer has an average molecular weight of 30,000 to 1,000,000, for example 30,000 to 500,000. Preferred PVME/MA copolymers include those under the GANTREZ brand from ISP (Wayne, N.J.). The PVME/MA copolymer may also act as an antibacterial enhancing agent if present in an antibacterial enhancing effective amount.

Hydrotropes are known in the art, and include compounds that solubilizes hydrophobic compounds in aqueous solutions. Hydrotropes are low molecular weight amphiphilic compounds which resemble surfactants in as much as they have hydrophilic groups, and, in surfactant terms, what maybe described as a low molecular weight hydrophobe. The hydrophilic group is may be attached to an organic moiety that is too short a group to confer true surface active properties. Hydrotropes useful in the present invention may include aromatic sulfonates, aromatic phosphate esters, di and polycarboxylates, polyglycols, and alcohols, including polyhydric alcohols. Hydrotropes useful in the present invention have a HLB value of from 7 to 18. Although any hydrotrope may be useful in the present invention (preferably GRAS), the hydrotrope may have a HLB value similar to that of the hydrophobic phase, and thus, the exact hydrotrope useful in the compositions will be dependent upon the composition of the hydrophobic phase. Preferably, the HLB of the coupling system is greater than the HLB of the hydrophobic phase, e.g., 10%, 15%, 20%, or 30% greater than the HLB of the hydrophobic phase. Methods of determining HLB is well known to those of skill in the art. The hydrotrope component in the present invention comprises one or more polyglycols and/or polyhydric alcohols, preferably a diol and/or a triol. Preferably, the coupling system comprises glycerine and propylene glycol. The exact ratio of glycerine and propylene glycol in the coupling system will depend on the desired HLB of the hydrotrope component of the present invention. As the hydrotrope lacks surfactant properties, the dispersion of the oil phase in the water is not thermodynamically stable, and an emulsion formed by mixing the two phases reverts back into separate and distinct phases immediately following mixing.

The compositions of the present invention incorporate one or more surfactants which are known in the art. Suitable surfactants include those which are reasonably stable throughout a wide pH range, for example, anionic, cationic, nonionic or zwitterionic surfactants. Preferred surfactants are nonionic surfactants. Preferably, the amount of surfactant in the compositions of the present invention is reduced to minimize the dispersion of the hydrophobic phase in the hydrophilic phase in the creation of emulsions which do not separate within 2 minutes from mixing the phases. It has been surprisingly found that minimizing the surfactant content and the presence of hydrotropes allows for efficient separation of the two phases. In one embodiment of the present invention, the oral compositions are free, or substantially free of surfactants, especially anionic, cationic, and zwitterionic surfactants. Nonionic surfactants may be use in limited quantities in the present invention. Such nonionic surfactants may be defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. The compositions of the present invention may contain from 0.0001% to 0.01% by weight of a surfactant.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The oral care compositions of the invention also may optionally include one or more chelating agents able to complex calcium found in the cell walls of the bacteria. Binding of this calcium weakens the bacterial cell wall and augments bacterial lysis.

One group of agents suitable for use as chelating or anti-plaque agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.5 wt. % pyrophosphate ions, 0.9-3 wt. %.

These compounds also contribute to preservation of the compositions by lowering water activity.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water

Water is present in the oral compositions of the invention. Water, employed in the preparation of commercial oral compositions should be deionized and free of organic impurities. Water commonly makes up the balance of the compositions and includes 10% to 90%, e.g., 40% to 70% by weight of the oral compositions. This amount of water includes the free water which is added plus that amount which is introduced with other materials such as with sorbitol or any components of the invention.

Humectants

Within certain embodiments of the oral compositions, it is also desirable to incorporate a humectant to reduce evaporation and also contribute towards preservation by lowering water activity. Certain humectants can also impart desirable sweetness or flavor to compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein.

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Enhancing oral health also provides benefits in systemic health, as the oral tissues can be gateways for systemic infections. Good oral health is associated with systemic health, including cardiovascular health. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1

Mouthwashes

Formulations of the invention are prepared with the following ingredients, weight percentages given with respect to the final dual phase formulation:

| Ingredients | Phase A (hydrophobic) | Phase B (hydrophilic) |
|---|---|---|
| Glycerin | — | 7.5 |
| Mineral oil | 12 | — |
| Sodium Fluoride | — | 0.05 |
| Sodium Saccharin | — | 0.08 |
| Citric Acid—Anhydrous | — | 0.01 |
| Monosodium Phosphate anhydrous | — | 0.05 |
| Surfactant | — | 0.1 |
| Flavor | 1.1 | — |
| Dye | 0.00012 | 0.004 |
| Potassium Sorbate | — | 0.1 |
| Sodium Benzoate | — | 0.11 |
| Cetyl Pyridinium Chloride | — | 0.05 |
| Water | — | Balance |
| pH | N/A | 5.5 |

To optimize the preservative system, different preservatives are substituted for potassium sorbate and/or sodium bezoate in the above formulation, and the characteristics of the formulation tested for antimicrobial efficacy of the hydrophilic phase, flavor impact, and aesthetics impact.

The Antimicrobial Preservation Effectiveness Test is used to determine the antimicrobial preservation effectiveness of water-based product formulations by means of a double challenge test. Products are developed to withstand microbial challenges introduced by normal consumer use. The test is run on an aged sample (13 weeks, 40° C.). The test uses two pools of microorganisms: bacteria/yeast and mold. The product is challenged at a 1% level at day 0 and at day 7.

Reduction of the inoculum is monitored over a 28 day period. The following are the acceptance criteria for mouth wash formulas.

Bacteria and Yeast must show a 99.9% reduction (3 logs) of the bacterial inoculum as determined by plate count on day 7 following each inoculation. No increase after day 7 of the second inoculation and for the remainder of the test within normal variation of the data.

Mold must show a 90.0% reduction (1 log) of the mold inoculum as determined by the plate count on day 14 following the second inoculation (day 21). No increase from day 14 to day 21 of the second inoculation of the test within normal variation of the data.

Flavor is evaluated via an organoleptic evaluation by trained flavorists.

Aesthetics are evaluated by a visual comparison to a control sample having the same types and levels of colorant and flavoring agents.

Results of the comparative testing are as follows, where a "✓" indicates criteria are met, and an "X" indicates criteria are not met.

| Preservative | Na benzoate @ 0.44% | Na benzoate @ 0.11% | 0.11% Na benzoate/ 0.1% K sorbate | 0.11% Na/ 0.001% MIT |
|---|---|---|---|---|
| Micro robustness | ✓ | X | ✓ | ✓ |
| In vitro eff. | ✓ | ✓ | ✓ | ✓ |
| Flavor impact | X | ✓ | ✓ | ✓ |
| Aesthetics impact | ✓ | ✓ | ✓ | ✓ |

Sodium benzoate provided acceptable microbial control alone at 0.44%, but this level had an adverse effect on flavor. When the amount of sodium benzoate was reduced, the level of microrobustness was reduced. The ideal formulation was a combination of sodium bezoate at 0.11% with low levels of potassium sorbate (0.1%) or methylisothiazolinone (MIT) (0.001%), which had good antimicrobial efficacy without detrimental effects on flavor or appearance of product.

What is claimed is:

1. A dual phase mouthwash comprising:

a hydrophilic phase, a hydrophobic phase, a hydrotrope, and an effective amount of a preservative comprising 0.1% sodium benzoate and 0.1% potassium sorbate by weight of the mouthwash, and wherein the hydrotrope component comprises glycerin and sorbitol, wherein the composition further comprises 0.01 to 0.1% cetylpyridinium chloride, and wherein the composition, when mixed, forms a temporary oil-in-water emulsion which breaks down and separates back into the hydrophobic and hydrophilic phases within 5 seconds to one hour following mixing.

2. The mouthwash of claim 1 wherein the hydrophobic phase comprises an oil selected from isopropyl myristate, mineral oil, an edible oil, and combinations thereof.

3. The mouthwash of claim 1 wherein the hydrophilic phase comprises the hydrotrope component.

4. The mouthwash of claim 3, wherein the hydrophobic phase comprises an oil selected from isopropyl myristate, mineral oil, an edible oil, and combinations thereof, and the mouthwash is ethanol-free.

5. The mouthwash of claim 1 further comprising a pyrophosphate.

6. The mouthwash of claim 1 further comprising a synthetic anionic polymeric polycarboxylate.

7. The mouthwash of claim 1 further comprising a fluoride ion source.

8. The mouthwash of claim 1 which is ethanol-free.

9. The mouthwash of claim 1 further comprising one or more of humectants, flavorings, and surfactants.

* * * * *